(12) United States Patent
Danford

(10) Patent No.: US 8,590,533 B2
(45) Date of Patent: Nov. 26, 2013

(54) ADJUSTABLE INHALATION RESISTANCE EXERCISE DEVICE

(76) Inventor: Casey Danford, Cadillac, MI (US)

(*) Notice: Subject to any disclaimer, the term of this patent is extended or adjusted under 35 U.S.C. 154(b) by 316 days.

(21) Appl. No.: 13/154,654

(22) Filed: Jun. 7, 2011

(65) Prior Publication Data

US 2012/0094806 A1    Apr. 19, 2012

Related U.S. Application Data

(60) Provisional application No. 61/393,044, filed on Oct. 4, 2010.

(51) Int. Cl.
*A62B 18/02* (2006.01)
*A62B 9/04* (2006.01)

(52) U.S. Cl.
USPC ............ 128/206.28; 128/201.22; 128/201.23; 128/202.27; 128/206.21

(58) Field of Classification Search
USPC ............ 128/201.22–201.24, 201.28, 202.27, 128/206.12, 206.15, 206.21, 206.23, 128/206.24, 206.28, 207.11; 601/41–43
See application file for complete search history.

(56) References Cited

U.S. PATENT DOCUMENTS

| | | | |
|---|---|---|---|
| 3,097,642 A * | 7/1963 | Russell | 128/205.17 |
| 3,633,575 A * | 1/1972 | Brumfield | 128/206.15 |
| 3,850,171 A | 11/1974 | Ball et al. | |
| 4,064,876 A * | 12/1977 | Mulchi | 128/206.15 |
| 4,221,381 A | 9/1980 | Ericson | |
| 4,549,543 A | 10/1985 | Moon | |
| 4,739,987 A | 4/1988 | Nicholson | |
| 4,961,420 A * | 10/1990 | Cappa et al. | 128/207.12 |
| 4,973,047 A | 11/1990 | Norell | |
| 5,167,819 A * | 12/1992 | Iana et al. | 210/474 |
| 5,848,589 A * | 12/1998 | Welnetz | 128/200.24 |
| 6,471,621 B2 | 10/2002 | Horstel et al. | |
| 6,554,746 B1 | 4/2003 | McConnell et al. | |
| 7,523,755 B2 * | 4/2009 | Richardson et al. | 128/207.12 |
| 2004/0146842 A1 | 7/2004 | Carlucci et al. | |
| 2009/0320848 A1 * | 12/2009 | Steindorf et al. | 128/206.21 |

* cited by examiner

*Primary Examiner* — Justine Yu
*Assistant Examiner* — Timothy Stanis
(74) *Attorney, Agent, or Firm* — Douglas S. Bishop

(57) ABSTRACT

A respiratory inhalation resistence exercise device with a separate air inlet and air outlet. A mask, which provides a substantially airtight perimeter seal during inhaling and lung expansion, is provided which covers at least the user's nose and mouth. Multiple air inlet inserts are provided for interchangeable use in the air inlet, allowing different rates and resistence to airflow, as provided. The device is held in place, hands free, by straps around the user's head. The device may also cover the entire face of a user, with lenses in eye openings for sight. The device may be utilized continually in vigorous exercise, without use of a mouthpiece, without significant protruding parts, without movable valves or parts, and held in place without limitation on the user's activity.

17 Claims, 4 Drawing Sheets

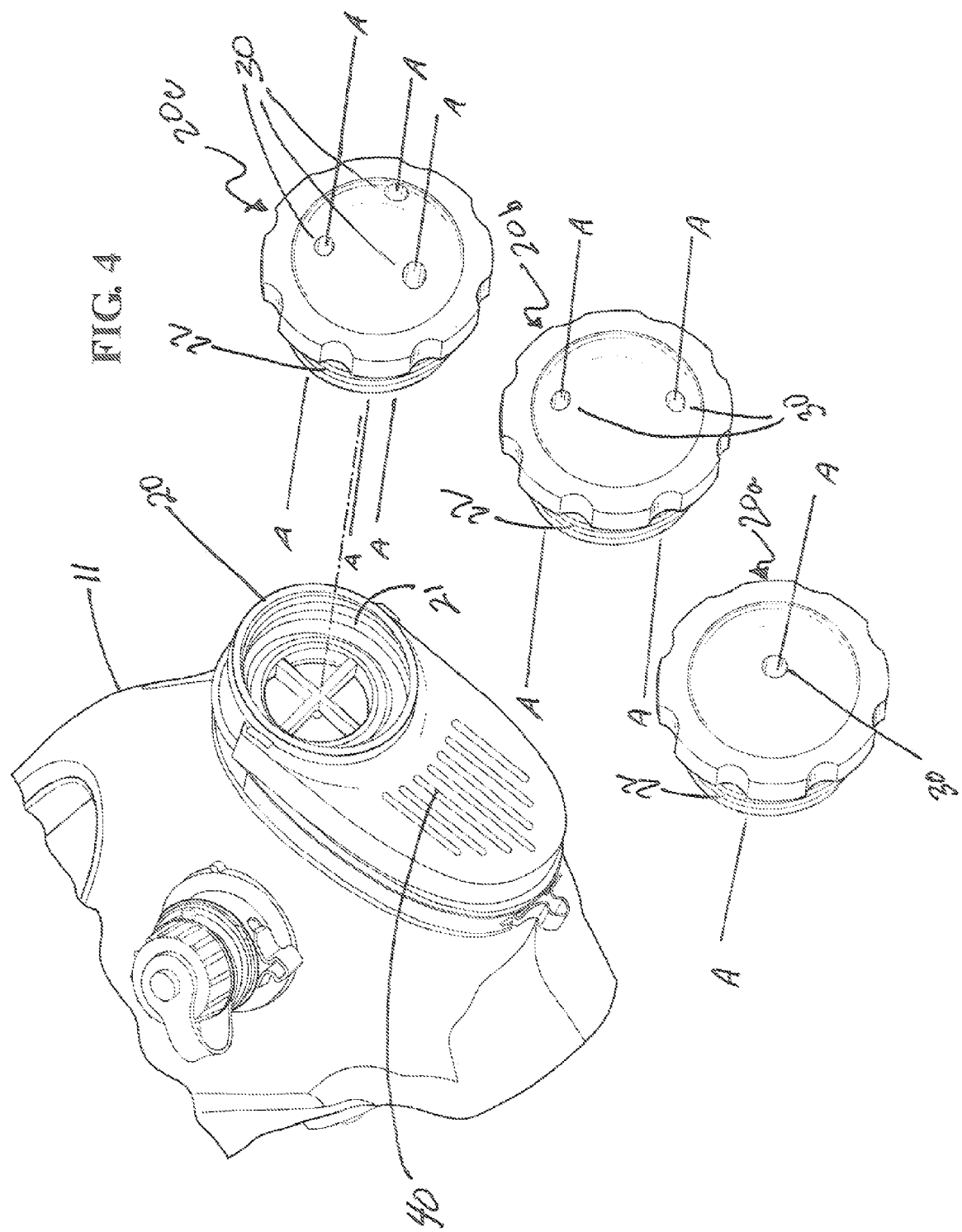

ADJUSTABLE INHALATION RESISTANCE EXERCISE DEVICE

CROSS-REFERENCE TO RELATED APPLICATIONS

The present application claims the priority of U.S. Provisional Patent Application Ser. No. 61/393,044, filed Oct. 4, 2010.

FIELD OF THE INVENTION

The device of the present invention relates to air inhalation resistance devices, generally, and, in particular, to such devices for use in the field of exercise, and extreme sports.

BACKGROUND OF THE INVENTION

It is generally known and understood, in athletic training and otherwise, that physical performance may be enhanced by the ability to deliver more oxygen to more active tissues, which in turn are the tissues which require more oxygen. What is often referred to as the bohr effect is a property of hemoglobin first described in 1904, which states that increasing concentration of protons and/or carbondioxide will reduce the oxygen affinity of hemoglobin. Increasing blood carbondioxide levels can lead to a decrease in pH because of the chemical equilibrium between protons and carbondioxide. Lower pH in the blood is suggestive of an increased carbondioxide concentration which, in turn, is suggestive of more active tissue, which requires more oxygen. According to the bohr effect, lower pH will cause delivery of greater concentrations of oxygen to the tissue. Separate and apart from the actual detailed scientific underpinning, it has long been generally known that high altitude training and training with less than optimum oxygen availability can enhance oxygen absorption capacity and, hence, athletic performance and endurance.

The use of breathing resistance training and the ability to vary the resistance, and difficulty of inhaling, is known. U.S. Pat. No. 6,554,746, to McConnell et al discloses an inspiratory muscle training device which has an opening for the passage of air to be both inhaled and exhaled and an inlet permitting air to be inhaled to enter the chamber and to pass through the opening. An adjustable valve is provided to vary the resistance to inhaling. U.S. Pat. No. 4,973,047, to Norell, discloses a therapeutic device for lung exercise which requires a mouthpiece, and has a rotatably adjustable air intake valve.

U.S. Pat. No. 4,549,543, to Moon, discloses an air filtering face mask and the concept of a flexible face piece which conforms to the shape of the face of the wearer, and is held in place by scraps or a harness device.

The prior art, however, does not provide a device, which does not require a mouth piece, or use the hands, and which further provides separate passages for inhaling and exhaling, which may be worn by a user, in intensely vigorous exercise, without impeding the nature of the exercise conducted. The present invention addresses the shortcomings of the prior art by providing a mask which conforms to the face of the user, providing a substantially airtight seal over the nasal and oral orifices, allowing free exhalation of air, without significant resistance, and a means for selectively varying the resistance of the air to be inhaled.

In athletic training, particularly in breathing resistance training, it becomes necessary and desirable to vary the amount of resistance to inhalation of air during vigorous exercise. The prior art, to the extent that it addresses the variability of air intake resistance, does so primarily by adjustable valves, which may include springs or other moving parts, or protruded valves which are twisted, all of which have the propensity to not function properly, or to be more susceptible to damage during vigorous exercise.

SUMMARY OP THE INVENTION

The respiratory inhalation resistance exercise device of the disclosed invention primarily consists of a face piece, or mask, which covers, at a minimum, the nostrils and mouth of a user, with a face conforming seal around them. The purpose of the conforming seal, or portion of the mask which conformably contacts the user's face continually around at least the nostrils and mouth, is to provide a substantially airtight seal during inhalation, so that air may only be inhaled through the air intake opening, which is described below. In practice, the device may be utilized with a piece which covers only the nose and the mouth or, in the embodiment shown in the drawings, may be a standard gas mask type assembly which covers the entire face of the user, contacting the user's forehead, face, and beneath the user's chin, basically to provide a substantially airtight seal. A separate internal substantially airtight seal around the nostrils and mouth may be provided as well. The device has separate air inlet and outlet openings. The outlet opening is a one-way valve, of any standard construction, which may include a movable diaphragm, which allows air to be exhaled, but closes and prevents inhalation through that opening. Such diaphragms are commonly known, and are "shelf-type" items. The air inhalation opening is an opening into which a series of plugs may be inserted, and held in place. Each of the plugs has a differently sized opening, or openings, to allow, for each plug, a different rate of airflow and a concurrent different resistance to inhalation when the user inhales. The differently sized plugs, which are removably and interchangeably insertable into the air intake opening, may be configured to be turned into place by means of reciprocal threads, on or in the opening, and on or in the individual plugs, although snap mechanisms or other alternative means, which would hold the plugs in place during exercise, could be used without prejudice to the device's function. The device is held in place on the user's face by a harness, or straps, which are attached to its outer edges, and hold the outer edge, or other portion of the mask, in continued conforming contact with the user's face, performing the stated function of keeping a substantially airtight seal over the user's nostrils and mouth. In practice, the differing rate of airflow of each plug may be accomplished by differing numbers of the air openings, or tubular perforations, which extend from the exterior of the plug, into the cavity created by the mask over the user's nose and mouth. Whether a differing number of such openings, or a different sized opening, or combination of these two options, is employed, the advantage is the interchangeability of the different plugs, each plug providing a different level of resistance to breathing, and air and oxygen intake, by the user during exercise.

A particular advantage of device is that it provides the ability for a user to vary the effort required to inhale oxygen during a workout, without requiring a mouth piece, without requiring moving parts or adjustable or protruding valves, in a device which essentially allows the user to exercise normally.

Other objects, advantages and novel features of the invention will be set forth and will become apparent in the detailed description which follows, with reference to the accompanying drawings.

BRIEF DESCRIPTION OF THE DRAWINGS

FIG. 4 is a view of the air inlet portion of the device showing three separate inserts, with varying numbers of apertures, by which the user may vary the air intake resistance.

DETAILED DESCRIPTION OF THE PREFERRED EMBODIMENT

As previously described, the present invention is an adjustable inhalation resistance exercise device 10. Use of the device and positioning thereof over a user's face are generally shown by FIGS. 1, 2 and 3 of the drawings.

Figure 1:
FIG. 1 discloses a perspective view of the device, worn by a user in vigorous exercise, including an optional liquid intake feature.
Figure 2:
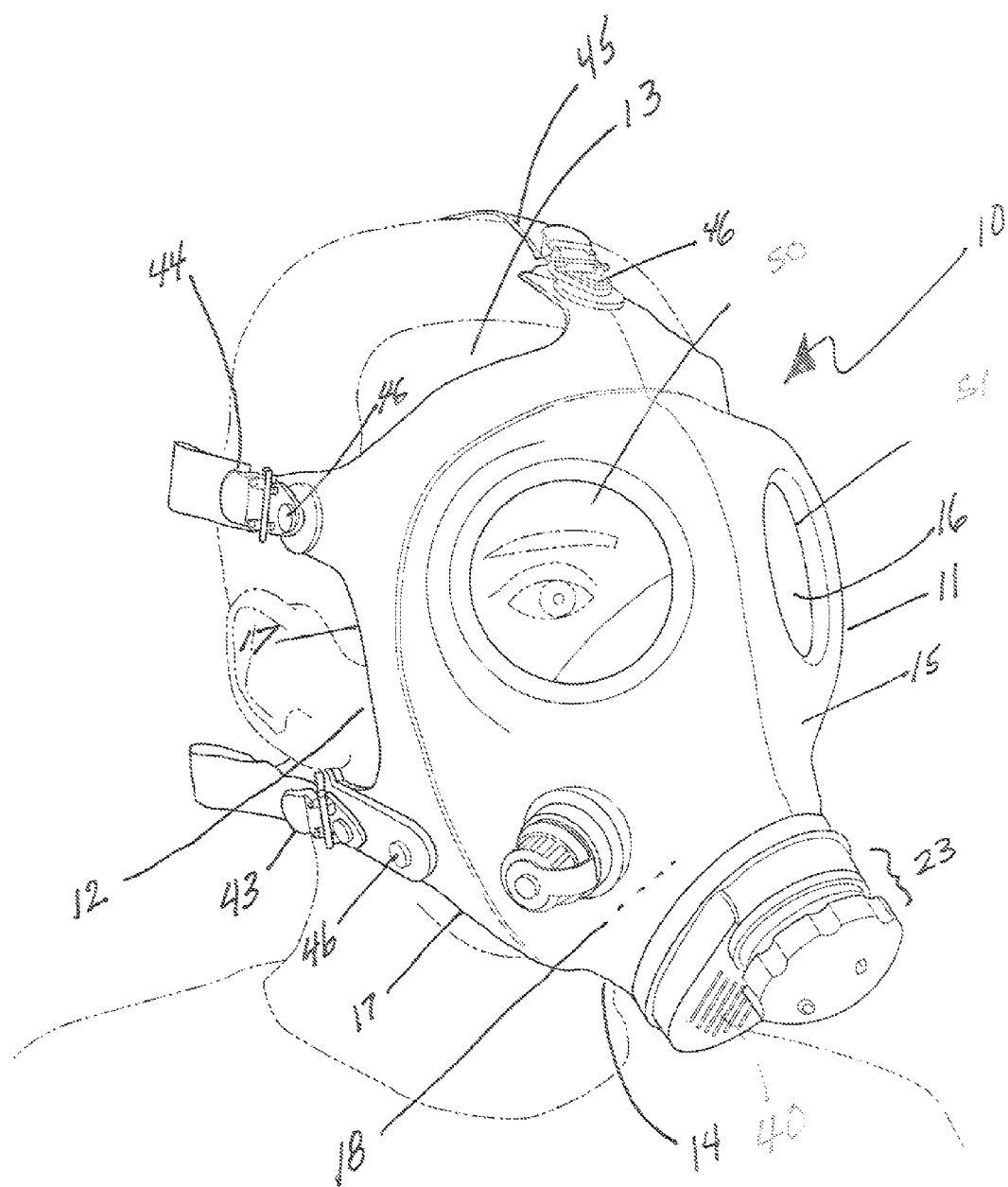
FIG. 2 is a close up of the device, worn on the face of user, in perspective, showing the relative relationship of the straps, and the device, to the user's face.
Figure 3:
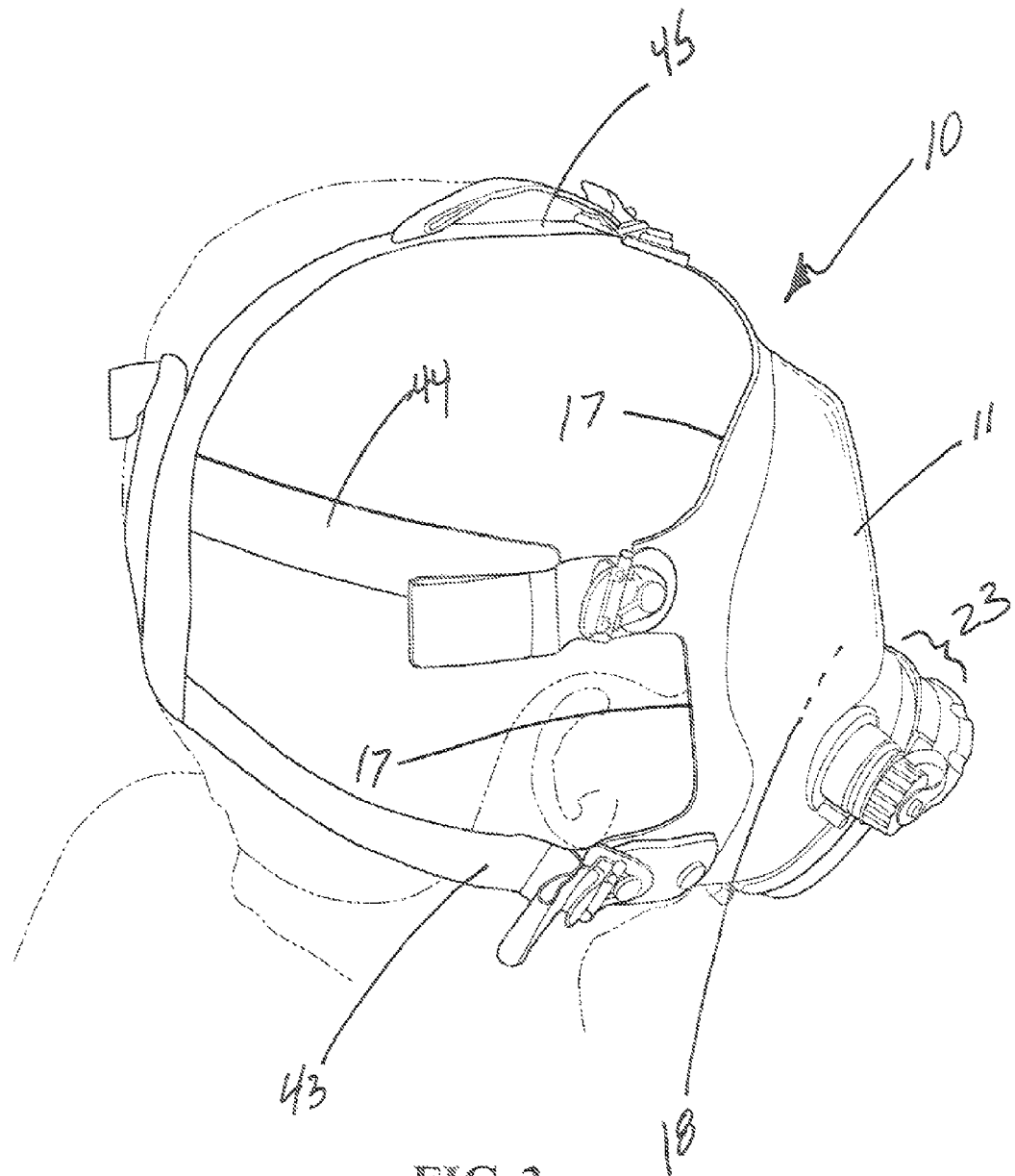
FIG. 3 is a side view of the device as worn by a user showing the strap attachment.

The device 10 has a primary mask or face piece 11 normally comprised of rubber, pliable plastic or material of like flexible properties and is generally seamless as shown in FIGS. 1-3 other than as necessary for features described below. In practice, a shelf item gas mask may be used as the face piece 11.

While the demonstrated embodiment of the device 10 shows a face piece 11 which covers the entire face of a user contacting the side of the user's face 12 as shown in FIG. 3 and maintaining continual conforming contact against the user's forehead 13 and under the user's chin 14 as shown in FIGS. 1 and 2, the device may service its intended novel function in any design which covers the user's nostrils and mouth, to provide a substantially airtight perimeter seal while inhaling.

The mask or face piece 11 has an exterior surface 15 and a corresponding interior surface 16. It has an outer or marginal edge including interconnected sections 17, 17', 17" et seq., which is continual and is conformable to continual uninterrupted contact with the user's face along the entire marginal edge 17, whether this edge covers the entire face of the user including contacting with the face 12, forehead 13 and under the chin 14 of the user as shown on FIGS. 1-3 of the drawings or is conformed simply to maintain continual marginal contact along the edge sections 17, 17', 17" of the user's face 12.

As demonstrated by FIGS. 1-3, the mask or face piece 11 provides a cavity 18 within its interior surface 16 over at least the nostrils and face of the user. The cavity created within the continual conforming contact may be not only entirely along the marginal edge 17, 17', 17" but, even in embodiments such as that shown in the drawings, face piece 11 may be conformed to provide such continual contact, even within the mask itself, to cover the nose and mouth areas of the user, but separate them from the balance of the interior of the mask, such as the eye openings.

This cavity 18 over the nostrils and mouth allows a user to utilize the device 10 inhaling and exhaling freely, without use of a mouthpiece or other contact with either the nostrils or mouth.

As most clearly shown in FIG. 4, an air intake opening or orifice 20 is provided to allow air to be drawn into die cavity 18 when the user inhales. Opening 20 in a standard gas mask type assembly is normally configured to removably hold a filtering device, oxygen canister or hose.

As one primary novel feature, the device 10 includes an infinite number of perforated plugs 20, and, in the demonstrated embodiment, three plugs, 20a, 20b and 20c. Opening 20 has a circular threaded interior 21. Plugs 20a, 20b and 20c are all correspondingly threaded on a lower, circular extension shown at 22, 22' and 22" respectively so as to be rotatably inserted and removably affixed in a mated relationship 23 within opening 20.

Each plug member 20 has one or more tubular, perforations at 30, 30' and 30" extending therethrough as demonstrated on FIG. 4 on lines A-A, A-A' and A"-A" with the total cross sections of all perforations 30, 30' and 30" in a plug 20a, 20b or 20c providing a defined area and, consequently, a permitted volume of air flow. In practice, the perforations may be of any shape so long as they are hollow and extend through the plug 20. Likewise, the air flow permitted by each plug 20 may be provided either by varying the size of perforation 20, increasing the number of perforations 20, or some combination thereof. As shown in FIG. 4, the different plugs 20 vary air flow by use of an ascending number of perforations 30—one in plug 20a, two in plug 20b and three in plug 20c, but the device is not limited to this number or sequence.

The device 10 also has a separate air outlet 40 for exhaling. As shown in closeup in FIG. 4, this outlet 10 may be in close proximity to opening 20, but is separate. A standard gas mask relief valve or any known air exhaust means allowing only a one way flow outward through the air outlet 40 will suffice and the device 10 is not limited by any particular variation thereof. Air may also be exhaled back through opening 20 in addition to the outlet 40.

In standard gas mask applications and in the embodiment shown, the primary mask application has eye openings 50 and 51 which contain transparent lenses for sight by the user.

Straps 43, 44 and 45 separate the various edge sections 17, 17', and 17" and are used to attach to the marginal edge of the face piece 11 of the device 10. These straps each have a first and second end and may be permanently attached to face piece 11 and utilize stretchable properties for donning by a user or they may be attached to the face piece 11 by removable means such as snaps 46, 46', 46" or any other suitable engagement structure such as additional clips or straps (not shown). Any other appropriate means, such as VELCRO® fasteners (commonly known as hook and loop) would also suffice.

The marginal edge 17, in keeping in contact with the face 12, forehead 13, under the chin 14 of the user may maintaining such contact in varying degrees of width and the conformable contact may extend for varied distance from the actual perimeter of edge 17, the only requirement being that the conformable contact remains continuous at some point between edge 17 and cavity 18.

The inner surface 16 and outer surface 15 of the face piece 11 may, as shown in FIG. 1, be fitted with a further opening 52, which may be kept in closed position, or configured with a hose attachment 53, which penetrates into cavity 18, to allow the user to intake fluid from a separate container 54 during exercise. This additional feature, however, is not necessary for the operation of the invention, and is only shown as an additional feature which may be incorporated. The primary requirement of the unitary conforming edge, whether it be located along the exterior of the entire face piece 11, or interior of edge 17, to simply provide a unitary conforming contact over the nose and mouth, to ensure that the device 10, during the time in which the user inhales, provides a substantially airtight seal, to require that all air, and contained oxygen, inhaled by the user during exercise, to be imported into cavity 18 through the total area of the one or more perforations 30 extending through the plug(s) 20 in direction A-A.

Having described my invention, other and additional and preferred embodiments will become apparent to those skilled in the art to which it pertains, and without deviating from the scope of the appended claims.

I claim:

1. A respiratory training device, comprising:
    a primary face piece having an interior surface and an exterior surface, and continual marginal edge;
    said edge adapted to being conformable to continual contact with the face of the user;
    said primary face piece further defining an interior cavity adapted to extend over the nostrils and mouth of the user and further defining an internally thread air intake orifice;
    a plurality of plug members conformably and alternatively mateable with said orifice, each of said plug members being externally threaded and interchangeably mateable with said orifice;
    each plug member consisting of up to three individual apertures defined through a surface thereof, each of said apertures defining a cross sectional area;
    a one direction air exhaust means located on said primary face piece; and
    said marginal edge of said primary face piece adapted to being held in continual contact with the face of the user.

2. The invention of claim 1, where a total cross sectional area defined by a number of apertures varies for each insert.

3. The invention of claim 1, wherein the primary face piece is adapted to cover the entire face of user.

4. The invention of claim 3, wherein said primary face piece further includes at least one viewing aperture defined by at least one transparent lens mounted to said face piece.

5. The invention of claim 1, further comprising at least one strap for adapting to hold the device conformably against the face of the user.

6. The invention of claim 5, further comprising a plurality of straps extending from said continual marginal edge, each of said strap being affixed at extending ends by a snap mechanism to further locations along said continual marginal edge.

7. The invention of claim 1, wherein said primary face piece is formed of flexible material.

8. The invention of claim 1, wherein the continual marginal edge is adapted to extend below the chin of the user.

9. The invention of claim 1, wherein the primary face piece is adapted to being conformable to continual contact with the face of the user, at a defined distance interior of the continua marginal edge.

10. The invention of claim 1, wherein the interchangeable plug members are mateable with the air intake orifice by a clip means.

11. A respiratory training device comprising a standard gas mask type assembly including at primary face mask piece having an interior and exterior surface defined in an interior cavity adapted to being placed over the nostrils and mouth and face and eye areas of the user, the interior surface being substantially air tight by adapting to conform to the face, head and chin of a user by establishing continual contact with the face, head and chin region of the user proximate tire marginal edge of the mask;
    where such mask has a single air intake orifice, configured to mateably accent one of either a filtering device, or hose, with the mask farther having one directional air exhaust supply located on the primary face piece, and further comprising:
    a plurality of plug members conformably and alternatively mateable with the air intake orifice;
    each plug member consisting of up to three individual apertures defined through a surface thereof, each of said apertures defining a cross sectional area; and
    where each plug member defines a different total cross sectional area defined by the total number of apertures provided.

12. A respiratory training device, comprising:
    a primary face piece having an interior surface and an exterior surface and a continual marginal edge;
    said continual marginal edge adapted to being conformable to continued contact with the face of the user;
    said primary face piece further defining an interior cavity adapted to extend over the nostrils and mouth of the user and further defining an air intake orifice;
    said air intake orifice having a defined area and a permitted volume of air flow;
    a plurality of plug members conformably and alternatively mateable with said orifice, each of said plug members consisting of up to three individual apertures defined through a surface thereof, each of apertures defining a cross sectional area and establishing an adjusted airflow resistance during inhalation;
    a one-direction air exhaust means located on said primary face piece; and
    the marginal edge of said primary face piece adapted to being in continual contact with the face of the user.

13. The invention of claim 12, further comprising at least one strap having a first end and a second end, with both first end and second end attached at separate points to said primary face piece.

14. An inhalation resistance exercise device, comprising:
    a flexible face mask adaptable to be secured about a wearers head such that said mask overlays and defines an interior cavity with the nostrils and mouth of the wearer while establishing an airtight perimeter seal with the wearers face; and
    a plurality of plugs alternately engageable with an orifice defined in said body, said plugs each consisting of up to three individual apertures defined through a surface thereof, each of said apertures defining a cross sectional area exhibiting an adjusted airflow resistance during inhalation by the wearer combined with substantially resistance free exhalation.

15. The exercise device as described in claim 14, further comprising at least one strap extending between opposite edges of said mask.

16. The exercise device as described in claim 14, further comprising a second orifice in said mask to which is engaged a hose attachment for communicating a fluid to said interior cavity.

17. The exercise device as described in claim 14, further comprising a unidirectional airflow air outlet incorporated in to said mask for assisting in wearer exhalation.

* * * * *